US00PP16035P3

(12) United States Plant Patent
Lintott

(10) Patent No.: US PP16,035 P3
(45) Date of Patent: Oct. 11, 2005

(54) *CHRYSANTHEMUM* PLANT NAMED 'JENNY WREN CRIMSON'

(50) Latin Name: *Chrysanthemum morifolium*
Varietal Denomination: Jenny Wren Crimson

(75) Inventor: Keith G. Lintott, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 10/692,919

(22) Filed: Oct. 24, 2003

(65) Prior Publication Data

US 2004/0083519 P1 Apr. 29, 2004

Related U.S. Application Data

(60) Provisional application No. 60/421,389, filed on Oct. 25, 2002.

(51) Int. Cl.[7] ..... A01H 5/00

(52) U.S. Cl. ..... Plt./293

(58) Field of Search ..... Plt./293

(56) References Cited

U.S. PATENT DOCUMENTS

PP6,888 P 6/1989 Mack ..... Plt./82
PP10,213 P 1/1998 Wain ..... Plt./76

OTHER PUBLICATIONS

Royal Van Zanien Garden Mum Catalog 2002 listing *Chrysanthemum* variety 'Jenny Wren Crimson' at pp. 9 and 11 (color picture) and 14. The catalog also lists parent variety 'Jenny Wren' at pp. 9 and 11 (color picture) and 14.

*Primary Examiner*—Anne Marie Grunberg
*Assistant Examiner*—Anette H Para
(74) *Attorney, Agent, or Firm*—Winston & Strawn LLP

(57) ABSTRACT

A new variety of *Chrysanthemum* plant named 'Jenny Wren Crimson,' having a large domed canopy of bright crimson decorative flowers that have very good weather resistance properties.

1 Drawing Sheet

Latin name of the genus and species: Botanical classification: *Chrysanthemum morifolium.*

Variety denomination: The new *Chrysanthemum* variety denomination is 'Jenny Wren Crimson.'

BACKGROUND OF THE INVENTION

The present invention comprises a new and distinct cultivar of *Chrysanthemum* botanically known as *Chrysanthemum morifolium,* and referred to by the cultivar name 'Jenny Wren Crimson.'

'Jenny Wren Crimson,' identified as 30017-2, originated from a naturally occurring whole plant mutation grown in a controlled planting of the variety 'Jenny Wren' (U.S. Plant Pat. No. 10,213) in Chichester, West Sussex, United Kingdom. The new variety 'Jenny Wren Crimson' has been asexually reproduced by vegetative cuttings in Chichester, West Sussex, United Kingdom and the distinguishing characteristics are retained through successive generations of asexual reproduction.

BRIEF SUMMARY OF THE INVENTION

'Jenny Wren Crimson' is a garden type of *Chrysanthemum* plant variety having a domed canopy of bright crimson decorative flowers.

Comparison with Parent

Plants of the new *Chrysanthemum* variety 'Jenny Wren Crimson' are similar to the parent variety 'Jenny Wren' in plant habit and growth rate. In side-by-side comparisons in Chichester, West Sussex, United Kingdom, under commercial practice, plants of the new *Chrysanthemum* variety 'Jenny Wren Crimson' differed from plants of the parent 'Jenny Wren' in the following characteristic.

1. The new variety 'Jenny Wren Crimson' produces crimson flowers whereas the parent 'Jenny Wren' produces purple flowers.

Comparison with Other Varieties

Plants of the new *Chrysanthemum* variety 'Jenny Wren Crimson' are dissimilar to the variety 'Bravo' (U.S. Plant Pat. No. 6,888) in plant habit and growth rate. In side-by-side comparisons in Chichester, West Sussex, United Kingdom, under commercial practice, plants of the new *Chrysanthemum* variety 'Jenny Wren Crimson' differed from plants of the cultivar 'Bravo' in the following characteristics.

1. The new variety 'Jenny Wren Crimson' produces more and larger flowers than 'Bravo.'
2. The new variety 'Jenny Wren Crimson' has a more domed and round habit than 'Bravo.'
3. The new variety 'Jenny Wren Crimson' is usually more vigorous than 'Bravo.'

BRIEF DESCRIPTION OF ILLUSTRATION

Typical specimens of the plant and flowers for the new *Chrysanthemum* variety 'Jenny Wren Crimson' are shown in the accompanying digital photograph. The colors shown are as true as possible within the usual limits of this kind of illustration.

FIG. 1 is a whole plant view of the new variety 'Jenny Wren Crimson' grown in a pot. The plant shown in the illustration is 63 days from the commencement of planting outdoors in mid-June.

DETAILED BOTANICAL DESCRIPTION

The following description of the new *Chrysanthemum* variety 'Jenny Wren Crimson' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 70° F. to 75° F. during the day under natural light conditions. The plants were grown outdoors in mid-June in 4 liter pots using a loamless compost. No growth retardants were used. To produce a commercial product the plants may be pinched once with the center bud removed. The typical container size for commercial growth is 4 liters (8"). It has been observed that the shelf life of the new variety is about 30 days with a response time of about 9 weeks natural season. The new variety is suitable for growth in a temperature range of 50° F. to 75° F.

The new variety may be produced as a pot plant. The following description is with respect to a plant produced as a garden pot plant. In the description of this new *Chrysanthemum* variety, color values have been taken from The Royal Horticultural Society Colour Chart (R.H.S.C.C.).

Plant

Plant type: Pot.
Habit: Domed — Round.
Height: 45 cm.
Width: 55–60 cm.
Branching characteristics: Curving and Free Branching.
Length of lateral branches: 16–35 cm.
Number of breaks from pinch: 7–9.
Stem color: Near 147A.
Response time: 63 days natural season.
Vigor: Medium/Tall.
Shelf life: Near 30 days.
Disease (susceptibility/resistance observed): None observed to date.
Pest (susceptibility/resistance observed): None observed to date.
Growth retardant type and treatment: No treatment necessary. The plants were grown for 9 weeks in natural season conditions.
Propagation:
*Type.*—Vegetative Propagation via Stem Cuttings.
*Time to rooting.*—12 days with soil temperatures of 70° F.
*Rooting habit.*—Fine and Fibrous.

Foliage

Number of leaves per lateral branch: 7–9.
Compound or single: Single.
Arrangement of leaves: Alternate.
*Shape of leaf.*—Typically 5 lobed ovate.
*Size of leaf.*—Width (cm): 2.8–5. Length (cm): 4.5–8.
*Leaf apex.*—Acute.
*Base.*—Obtuse.
*Attachment.*—Petioled.
*Aspect.*—Slightly Undulating.
*Margin.*—Palmately Lobed.
*Surface characteristics.*—Top: Slightly Pubescent. Bottom: Slightly Pubescent.
Petiole:
*Color.*—Near 146A.
*Length.*—1–1.8 cm.
*Diameter.*—0.2–0.4 cm.
Venation: Net prominent mid-vein at underside.
*Color.*—Upper side: near 146C. Under side: near 146C.
Color:
*Mature leaf, upper side.*—Near 147A; under side: near 147B.
*Young leaf, upper side.*—Near 147A; under side: near 147B.

Flower

Flower appearance: Matte.
Flower type: Decorative.
Flower form: Slightly Incurving.
Flower shape: Round.
Flowering habit: Cyme.
Number of blossoms per branch: 5–7.
Inflorescence form: Corymibiform.
*Depth of fully expanded blossoms.*—3 cm.
*Diameter of fully expanded blossoms.*—4.5–5.5 cm.
Phyllaries:
*Number.*—20–22.
*Color.*—Near 138A.
*Length.*—0.8–1 cm.
*Width.*—1.5–2 mm.
*Texture/appearance.*—Pubescent.
Pedicel:
*Length.*—Terminal: 4–6 cm; lateral: 5–7 cm.
*Color.*—Near 147C.
*Surface.*—Pubescent.
*Habit.*—Slightly Curving.
*Strength.*—Medium/Strong.
Peduncle:
*Length.*—Terminal: 5–7 cm; lateral: 6–8 cm.
*Diameter.*—0.4–0.5 cm.
*Color.*—Near 147A.
*Habit.*—Slightly curving.
*Surface.*—Slightly pubescent.
*Strength.*—Moderately strong.
Ray florets:
*Form/shape.*—Straight with oblong shape.
*Texture/appearance.*—Matte.
*Number per flower.*—180–195.
*Length.*—1.5–3 cm; Width: 3–5 mm.
*Apex.*—Rounded, Slightly Dentate.
*Base.*—Tubular/Tapered.
*Margin.*—Entire.
Disc florets:
*Form/shape.*—Cylindrical.
*Texture/appearance.*—Shiny.
*Number per flower.*—2 observed.
*Length.*—5 mm; Width: <1 mm.
*Diameter of disc.*—1 mm.
Fragrance: None.
Flower bud (at onset of color):
*Length.*—1 cm.
*Diameter.*—0.9 cm.
*Form/shape.*—Globular.
General flower color:
*1. Ray florets, upper side.*—Immature: near 181A. Mature: near 182A. Older/Fading: near 179A.

2. *Ray florets, under side.*—Immature: near 181A. Mature: near 182A. Older/Fading: near 179A.
3. *Disc florets.*—Immature: near 179B. Mature: near 179B. Older/Fading: near 179D.
4. *Bud.*—Near 181A.

Flower progression with age: Flowers fade uniformly with age and the petals roll to form tubes.

Reproductive Organs

Gynoecium present on Ray and Disc florets.
Ray florets per individual flower:
*Pistil number.*—35–40 observed.
*Stigma color.*—Near 144D.
*Stigma shape.*—Forked.
*Style color.*—Near 144D.
*Style length.*—1.5–2 mm.
Disc florets per individual flower:
*Pistil number.*—2.
*Stigma color.*—Near 144D.
*Stigma shape.*—Forked.
*Style color.*—Near 144D.
*Style length.*—1.5 mm.
Androecium not observed.
Fruit and seeds: None observed.

What is claimed is:

1. A new and distinct variety of *Chrysanthemum* plant, substantially as described and illustrated herein.

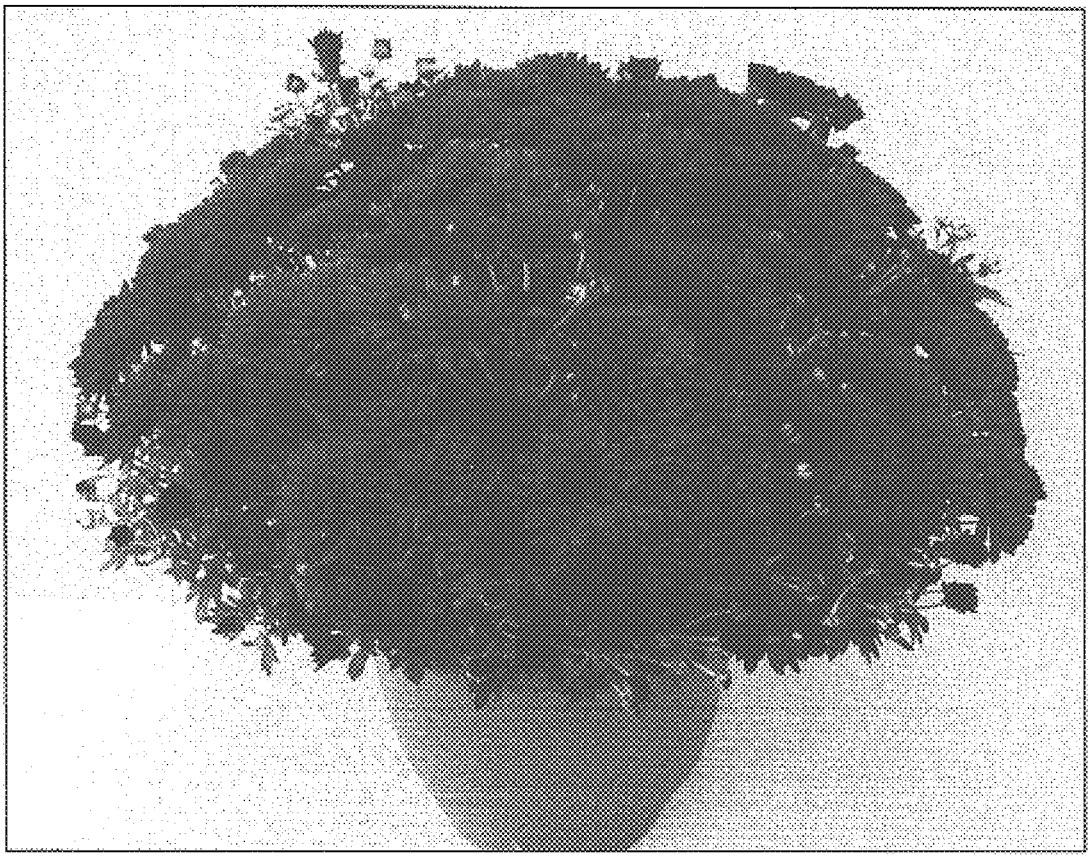

* * * * *